United States Patent
Krenzer

[11] 3,951,640
[45] Apr. 20, 1976

[54] HETEROCYCLIC THIADIAZOLYLUREAS

[75] Inventor: John Krenzer, Oak Park, Ill.

[73] Assignee: Velsicol Chemical Corporation, Chicago, Ill.

[22] Filed: Feb. 18, 1975

[21] Appl. No.: 546,637

Related U.S. Application Data

[62] Division of Ser. No. 387,051, Aug. 9, 1973, Pat. No. 3,901,902.

[52] U.S. Cl. .................................................. 71/90
[51] Int. Cl.² ........................................... A01N 9/22
[58] Field of Search ........................................ 71/90

[56] References Cited
UNITED STATES PATENTS

| | | | |
|---|---|---|---|
| 3,827,875 | 8/1974 | Krenzer | 71/90 |
| 3,856,503 | 12/1974 | Cebalo | 71/90 |
| 3,864,775 | 2/1975 | Krenzer | 71/90 |

*Primary Examiner*—Lewis Gotts
*Assistant Examiner*—Catherine L. Mills
*Attorney, Agent, or Firm*—Robert J. Schwarz; Dietmar H. Olesch

[57] ABSTRACT

This invention discloses new compounds of the formula

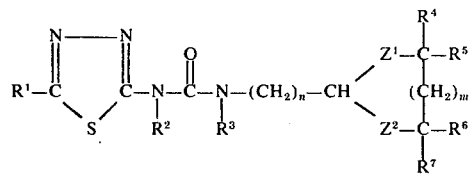

wherein $R^1$ is selected from the group consisting of alkyl, alkenyl, haloalkyl, cycloalkyl, alkoxy, alkylthio, alkylsulfonyl and alkylsulfinyl; $Z^1$ and $Z^2$ are independently selected from the group consisting of oxygen and sulfur; $R^2$, $R^3$, $R^4$, $R^5$, $R^6$ and $R^7$ are each selected from the group consisting of hydrogen and alkyl; $m$ is an integer from 0 to 2; and $n$ is the integer 1 or 2. The compounds of the above description are useful as herbicides.

2 Claims, No Drawings

HETEROCYCLIC THIADIAZOLYLUREAS

This application is a division of copending application Ser. No. 387,051, filed Aug. 9, 1973 now Pat. No. 3,901,902.

This invention relates to new compositions of matter and more specifically relates to new chemical compounds of the formula

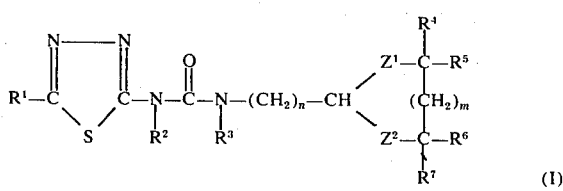

(I)

wherein $R^1$ is selected from the group consisting of alkyl, alkenyl, haloalkyl, cycloalkyl, alkoxy, alkylthio, alkylsulfonyl and alkylsulfinyl; $Z^1$ and $Z^2$ are independently selected from the group consisting of oxygen and sulfur; $R^2$, $R^3$, $R^4$, $R^5$, $R^6$ and $R^7$ are each selected from the group consisting of hydrogen and alkyl; $m$ is an integer from 0 to 2; and $n$ is the integer 1 or 2. The compounds of this invention are unexpectedly useful as herbicides.

In a preferred embodiment of the present invention $R^1$ is selected from the group consisting of lower alkyl, lower alkenyl, lower chloroalkyl, lower bromoalkyl, trifluoromethyl, cycloalkyl of from 3 to 7 carbon atoms, lower alkoxy, lower alkylthio, lower alkylsulfonyl and lower alkylsulfinyl; and $R^2$, $R^3$, $R^4$, $R^5$, $R^6$ and $R^7$ are each selected from the group consisting of hydrogen and lower alkyl. The term lower as used herein designates a straight or branched carbon chain of up to six carbon atoms.

The compounds of the present invention wherein $R^2$ is hydrogen can be prepared by reacting a thiadiazolyl isocyanate of the formula

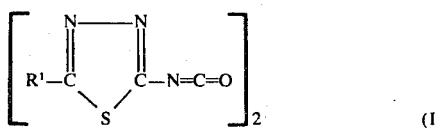

(II)

wherein $R^1$ is as heretofore described, with a compound of the formula

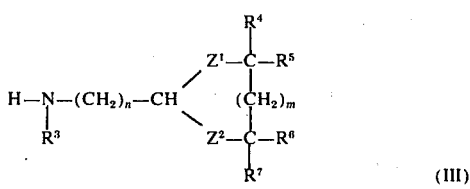

(III)

wherein $R^3$, $R^4$, $R^5$, $R^6$, $R^7$, $Z^1$, $Z^2$, $n$ and $m$ are as heretofore described. This reaction can be effected by adding the isocyanate dimer of formula II to a solution of the compound of formula III in an organic solvent such as benzene at room temperature with stirring. The reaction mixture can then be heated on a steam bath for a period of from about 5 to 60 minutes to ensure completion of the reaction. After this time the reaction mixture can be stripped of solvent under reduced pressure to yield the desired product as a residue. This product can be used as such or can be further purifed by conventional means.

The isocyanate dimer of formula II can be prepared by reacting an aminothiadiazole of the formula

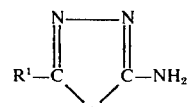

(IV)

wherein $R^1$ is as heretofore described, with phosgene. This reaction can be effected by adding a solution of phosgene in ethyl acetate to a solution or suspension of the aminothiadiazole in ethyl acetate at room temperature with stirring. After the addition is completed stirring can be continued for a period of up to about 18 hours to ensure completion of the reaction. The reaction mixture can then be purged with nitrogen to remove unreacted phosgene. The desired product can then be recovered by filtration if it forms as a precipitate or upon evaporation of the solvents used if soluble therein.

The compounds of formula III can be prepared by reacting a compound of the formula

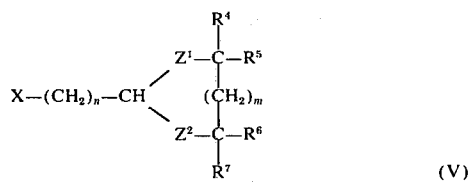

(V)

wherein X is chloride or bromine and $Z^1$, $Z^2$, $R^4$, $R^5$, $R^6$, $R^7$, $n$ and $m$ are as heretofore described with an amine of the formula

(VI)

wherein $R^3$ is as heretofore described. This reaction can be effected by adding the compound of formula V to a solution of the amine in a suitable solvent such as water or methanol. The mixture can then be stirred for a period of up to about 18 hours. After this time base such as sodium hydroxide is incrementally added and stirring is continued for an additional period of up to 18 hours. The desired product can then be recovered upon decantation of the organic phase if water is used as a solvent or upon evaporation of the solvent if an organic solvent is used. The resulting product can then be purified by conventional means.

The compounds of formula V can be prepared by reacting an acetal of the formula

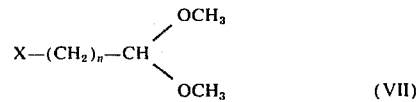

(VII)

wherein X and $n$ are as heretofore described, with a diol or dithiol of the formula

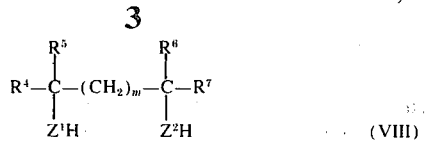

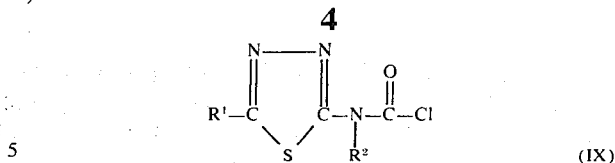

wherein $R^4$, $R^5$, $R^6$, $R^7$, $Z^1$, $Z^2$ and $m$ are as heretofore described. This reaction can be effected by combining the compound of formula VII with the compound of formula VIII in about equimolar amounts and in the presence of an acid catalyst, such as sulfuric acid or toluene sulfonic acid, under anhydrous conditions. The mixture can be heated at reflux for a period of from about 1 to 4 hours. After this time the reaction mixture can be distilled under reduced pressure to yield the desired product.

Exemplary diols and dithiols of formula VIII useful for preparing the compounds of formula V are ethandiol-1,2, propandiol-1,2, propandiol-1,3, butandiol-1,2, butandiol-1,3, butandiol-1,4, butandiol-2,3, pentandiol-1,2, pentandiol-1,3, pentandiol-1,4, pentandiol-2,3, pentandiol-2,4, 2-methylpentandiol-2,4, 2-methylpropandiol-1,2, 2-methylbutandiol-2,3, 3-methylbutandiol-1,3, hexandiol-1,2, hexandiol-1,4, hexandiol-2,3, hexandiol-2,4, hexandiol-2,5, hexandiol-3,4, 3-methylhexandiol-3,4, 3-ethylhexandiol-3,4, ethandithiol-1,2, propandithiol-1,2, propandithiol-1,3, butandithiol-1,2, butandithiol-1,3, butandithiol-1,4, butandithiol-2,3, pentandithiol-1,2 and the like.

Exemplary thiaziazoles of formula IV are 2-amino-5-methyl-1,3,4-thiadiazole, 2-amino-5-isopropyl-1,3,4-thiadiazole, 2-amino-5-t-buryl-1,3,4-thiadiazole, 2-amino-5-hexyl-1,3,4-thiadiazole, 2-amino-5-allyl-1,3,4-thiadiazole, 2-amino-5-hex-4-enyl-1,3,4-thiadiazole, 2-amino-5-chloromethyl-1,3,4-thiadiazole, 2-amino-5-bromomethyl-1,3,4-thiadiazole, 2-amino-5-trichloromethyl-1,3,4-thiadiazole, 2-amino-5-trifluoromethyl-1,3,4-thiadiazole, 2-amino-5-$\beta$-bromoethyl-1,3,4-thiadiazole, 2-amino-5-$\gamma$-chloropropyl-1,3,4-thiadiazole, 2-amino-5-cyclopropyl-1,3,4-thiadiazole, 2-amino-5-cyclobutyl-1,3,4-thiadiazole, 2-amino-5-cyclopentyl-1,3,4-thiadiazole, 2-amino-5-cyclohexyl-1,3,4-thiadiazole, 2-amino-5-cycloheptyl-1,3,4-thiadiazole, 2-amino-5-methoxy-1,3,4-thiadiazole, 2-amino-5-ethoxy-1,3,4-thiadiazole, 2-amino-5-propoxy-1,3,4-thiadiazole, 2-amino-5-butoxy-1,3,4-thiadiazole, 2-amino-5 -hexyloxy-1,3,4-thiadiazole, 2-amino-5-methylthio-1,3,4-thiadiazole, 2-amino-5-ethylthio-1,3,4-thiadiazole, 2-amino-5-butylthio-1,3,4-thiadiazole, 2-amino-5-hexylthio-1,3,4-thiadiazole, 2-amino-5-methylsulfonyl-1,3,4-thiadiazole, 2-amino-5-ethylsulfonyl-1,3,4-thiadiazole, 2-amino-5-propylsulfonyl-1,3,4-thiadiazole, 2-amino-5pentylsulfonyl-1,3,4-thiadiazole, 2-amino-5-hexylsulfonyl-1,3,4-thiadiazole, 2-amino-5-methylsulfinyl-1,3,4-thiadiazole, 2-amino-5-ethylsulfinyl-1,3,4-thiadiazole, 2-amino-5-propylsulfinyl-1,3,4-thiadiazole, 2-amino-5-butylsulfinyl-1,3,4-thiadiazole, 2-amino-5-hexylsulfinyl-1,3,4-thiadiazole, 2-methylamino-5-trifluoromethyl-1,3,4-thiadiazole, 2-ethylamino-5-trifluoromethyl-1,3,4-thiadiazole, 2-propylamino-5-trifluoromethyl-1,3,4-thiadiazole, 2-butylamino-5-trifluoromethyl-1,3,4-thiadiazole, 2-hexylamino-5-trifluoromethyl-1,3,4-thiadiazole and the like.

The compounds of this invention wherein $R^2$ is alkyl can be prepared by reacting a compound of formula III with a carbamoyl chloride of the formula wherein $R^2$ is alkyl and $R^1$ is as heretofore described. This reaction can be effected by combining about equimolar amounts of the compounds of formulae III and IX in an inert organic reaction medium such as benzene and in the presence of an acid acceptor such as tertiary amine or alkali metal carbonate or bicarbonate. The reaction mixture can be heated at temperatures of up to the reflux temperature of the mixture to ensure completion of the reaction. After this time the mixture is filtered to remove acid acceptor salts and the filtrate is stripped of solvent to yield the desired product. This product can be used as such or can be further purified by conventional means.

The compounds of formula IX can be prepared by reacting a compound of the formula

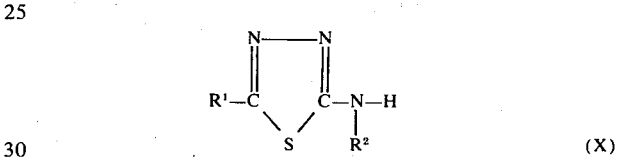

wherein $R^2$ is alkyl and $R^1$ is as heretofore described, with phosgene. This reaction can be effected by adding the thiadiazole of formula X to a solution of phosgene in an inert solvent such as benzene and thereafter heating the resulting mixture at reflux with stirring for a period of several hours until the reaction mixture becomes clear. After this time the mixture can be stripped of solvent to yield the desired product as the residue.

Suitable thiadiazoles of formula X useful for preparing the compounds of this invention are the exemplified thiadiazoles of formula IV which have in place of the 2-amino substituent a 2-methylamino, 2-ethylamino, 2-propylamino, 2-butylamino, 2-pentylamino or 2-hexylamino substituent.

The manner in which the compounds of the present invention can be prepared is more specifically illustrated in the following examples.

EXAMPLE 1

Preparation of 2-Trifluoromethyl-1,3,4-thiadiazol-5-yl Isocyanate Dimer

A saturated solution of phosgene in ethyl acetate (100 ml) was charged into a glass reaction vessel equipped with a mechanical stirrer. A slurry of 2-trifluoromethyl-5-amino-1,3,4-thiadiazole (45 grams) in ethyl acetate (300 ml) was added to the reaction vessel and the resulting mixture was stirred for a period of about 16 hours resulting in the formation of a precipitate. The reaction mixture was then purged with nitrogen gas to remove unreacted phosgene. The purged mixture was filtered to recover 48 grams of a white solid. This solid was recrystallized from dimethyl formamide to yield the desired product 2-trifluoromethyl-1,3,4-thiadiazol-5-yl isocyanate dimer.

EXAMPLE 2

Preparation of 2-Bromomethyl-1,3-dioxolane

The dimethyl acetal of 2-bromoacetaldehyde (290 grams) and ethandiol -1,2 (92 grams) were charged into a glass reaction vessel equipped with a mechanical stirrer, thermometer and reflux condenser. Hydrochloric acid (1.5 ml) was added to the flask and the raction mixture was refluxed for a period of about 2 hours. After this time the reaction mixture was distilled under reduced pressure to yield the desired product 2-bromomethyl-1,3-dioxolane.

EXAMPLE 3

Preparation of N-(1,3-Dioxolan-2-ylmethyl)-N-methylamine

A 40% by weight aqueous solution (100 ml) of methylamine and 2-bromomethyl-1,3-dioxolane (40 grams) were charged into a glass reaction vessel equipped with a mechanical stirrer. The reaction mixture was stirred for a period of about 18 hours. After this time sodium hydroxide (18 grams) was added with stirring over a period of about 4 hours. Stirring was then continued for an additional period of about 16 hours. The organic phase of the reaction mixture was then separated, was washed with aqueous potassium carbonate and dried over anhydrous magnesium sulfate. The dried product was then distilled under reduced pressure to yield the desired product N-(1,3-dioxolan-2-ylmethyl)-N-methylamine.

EXAMPLE 4

Preparation of N-(2-Trifluoromethyl-1,3,4-thiadiazol-5-yl)-N'-(1,3-dioxolan-2-ylmethyl)-N'-methylurea 2-Trifluoromethyl-1,3,4-thiadiazol-5-yl isocyanate dimer (3.1 grams) was added to a solution of N-(1,3-dioxolan-2-ylmethyl)-N-methylamine (2grams) in benzene (10 ml) contained in a glass reaction vessel equipped with a mechanical stirrer and thermometer. The mixture was heated on a steam bath for a period of about 1 hour. The mixture was then stripped of solvent under reduced pressure to yield a solid residue. The residue was recrystallized from an ether-pentane mixture to yield the desired product N-(2-trifluoromethyl-1,3,4-thiadiazol-5-yl)-N'-(1,3-dioxolan-2-ylmethyl)-N'-methylurea having a melting point of 114° to 115°C.

EXAMPLE 5

Preparation of 2-Chloromethyl-1,3-dioxolane

The dimethyl acetal of 2-chloroacetaldeyde (125 grams; 1.0 mole) and ethandiol-1,2 (62 grams; 1.0 mole) are charged into a glass reaction flask equipped with a mechanical stirrer, thermometer and reflux condenser. Toluene sulfonic acid (0.3 grams) is added to the flask and the reaction mixture is refluxed for a period of about 2 hours. After this time the reaction mixture is distilled under aspirator partial pressure to remove methanol, yielding the desired product 2-chloromethyl-1,3-dioxolane.

EXAMPLE 6

Preparation of N-(1,3-Dioxolan-2-ylmethyl)-N-ethylamine

A 40% by weight aqueous solution of ethylamine (100 ml) and 2-chloromethyl-1,3-dioxolane (35 grams) are charged into a glass reaction vessel equipped with a mechanical stirrer. The reaction mixture is stirred for a period of about 18 hours. After this time sodium hydroxide (18 grams) is added with stirring over a period of about 4 hours. Stirring is then continued for an additional period of about 16 hours. The organic phase of the reaction mixture is then separated, washed with aqueous potassium carbonate and dried over anhydrous magnesium sulfate. The dried product is then distilled under reduced pressure to yield the desired product N-(1,3-dioxolan-2-ylmethyl)-N-ethylamine.

EXAMPLE 7

Preparation of 2-t-Butyl-1,3,4-thiadiazol-5-yl Isocyanate Dimer

A saturated solution of phosgene in ethyl acetate (100 ml) was charged into a glass reaction vessel equipped with a mechanical stirrer. A slurry of 2-t-butyl-5-amino-1,3,4-thiadiazole (10 grams) in ethyl acetate (300 ml) was added to the reaction vessel and the resulting mixture was stirred for a period of about 16 hours resulting in the formation of a precipitate. The reaction mixture was then purged with nitrogen gas to remove unreacted phosgene. The purged mixture was then filtered to recover the desired product 2-t-butyl-1,3,4-thiadiazol-5-yl isocyanate dimer.

EXAMPLE 8

Preparation of N-(2-t-Butyl-1,3,4-thiadiazol-5-yl)-N'-(1,3-dioxolan-2-ylmethyl)-N'-ethylurea 2-t-Butyl-1,3,4-thiadiazol-5-yl isocyanate dimer (3grams) and a solution of N-(1,3-dioxolan-2-ylmethyl)-N-ethylamine (2 grams) in benzene (10 ml) are charged into a glass reaction vessel equipped with a mechanical stirrer and thermometer. The mixture is warmed on a steam bath with stirring for a period of about 1 hour. After this time the mixture is stripped of solvent under reduced pressure to yield a solid residue. The residue is recrystallized to yield the desired product N-(2-t-butyl-1,3,4-thiadiazol-5-yl) -N'-(1,3-dioxolan-2-ylmethyl)-N'-ethylurea.

EXAMPLE 9

Preparation of 2-Chloromethyl-1,3-dithiepane

The dimethyl acetal of 2-chloroacetaldehyde (125 grams; 1.0 mole) and butandithiol-1,4 (122 grams, 1.0 mole) are charged into a glass reaction vessel equipped with a mechanical stirrer, thermometer and reflux condenser. Toluene sulfonic acid (0.3 grams) is added to the reaction mixture and the mixture is refluxed for a period of about 2 hours. After this time the reaction mixture is distilled under aspirator pressure to yield the desired product 2-chloromethyl-1,3-dithiepane.

EXAMPLE 10

Preparation of N-(1,3-Dithiepan-2-ylmethyl)-N-methylamine

A 40% by weight aqueous solution of methylamine (100 ml) and 2-chloromethyl-1,3-dithiepane (50 grams) are charged into a glass reaction vessel equipped with a mechanical stirrer. The reaction mixture is stirred for a period of about 18 hours. After this time sodium hydroxide (18 grams) is added with stirring over a period of about 3 hours. Stirring is then continued for an additional period of about 16 hours. The organic phase of the reaction mixture is then separated, is washed with aqueous potasssium carbonate and dried over anhydrous magnesium sulfate. The dried product is then distilled under reduced pressure to yield the desired product N-(1,3-dithiepan-2-ylmethyl)-N-methylamine.

EXAMPLE 11

Preparation of N-(2-Methylthio-1,3,4-thiadiazol-5-yl)-N-methylcarbamoyl chloride 2-Methylthio-5-methylamino-1,3,4-thiadiazole (0.1 mole) and a solution of phosgene (0.11 mole) in benzene (200 ml) are charged into a glass reaction vessel equipped with a mechanical stirrer and reflux condenser. The reaction mixture is heated at reflux for a period of about 4 hours. After this time the reaction mixture is stripped of benzene and unreacted phosgene to yield the desired product N-(2-methylthio-1,3,4-thiadiazol-5-yl)-N-methylcarbamoyl chloride.

EXAMPLE 12

Preparation of N-(2-Methylthio-1,3,4-thiadiazol-5-yl)-N-methyl-N'-(1,3-dithiepan-2-yl)urea N-(2-Methylthio-1,3,4-thiadiazol-5-yl)-N-methylcarbamoyl chloride (0.05 mole), N-(1,3-dithiepan-2-ylmethyl)-N-methylamine (0.05 mole), triethylamine (0.07 mole) and benzene (200 ml) are charged into a glass reaction vessel equipped with a mechanical stirrer, thermometer and reflux condenser. The reaction mixture is then heated at reflux for a period of about 5 hours. After this time the mixture is cooled to room temperature and is filtered. The filtrate is washed with water and dried over anhydrous magnesium sulfate. The dried solution is then stripped of benzene under reduced pressure to yield the desired product N-(2-methylthio-1,3,4-thiadiazol-5-yl)-N-methyl-N'-methyl-N'-(1,3-dithiepan-2-yl)urea.

EXAMPLE 13

Preparation of 2-Chloromethyl-1,3-dioxane

The dimethyl acetal of 2-chloroacetaldehyde (125 grams; 1.0 mole) and propandiol-1,3 (76 grams; 1.0 mole) are charged into a glass reaction vessel equipped with a mechanical stirrer, thermometer and reflux condenser. Toluene sulfonic acid (0.3 grams) is added to the reaction mixture and the mixture is refluxed for a period of about 3 hours. After this time the reaction mixture is distilled under aspirator pressure to yield the desired product 2-chloromethyl-1,3-dioxane.

EXAMPLE 14

Preparation of N-(1,3-Dioxan-2-ylmethyl)amine

Cooled 2-chloromethyl-1,3-dioxane (0.2 mole) dissolved in absolute alcohol (150 ml) and liquid ammonia (2.0 moles) are charged into a pressure vessel. The vessel is sealed and heated to a temperature of about 120°C, with shaking for a period of about 12 hours. The pressure vessel is cooled and the ammonia is allowed to escape. The reaction mixture is then combined with absolute ethanol (150 ml) and the resulting solution is filtered. The filtrate is stripped of alcohol and is dissolved in ether. The ether solution is filtered to remove inorganic salt. The filtered solution is stripped of ether on a steam bath under reduced pressure to yield the desired product N-(1,3-dioxan-2-ylmethyl)amine.

EXAMPLE 15

Preparation of N-(2-Methylsulfonyl-1,3,4-thiadiazol-5-yl)-N-methylcarbamoyl chloride 2-methylsulfonyl-5-methylamino-1,3,4-thiadiazole (0.1 mole) and a solution of phosgene (0.11 mole) in benzene (200 ml) are charged into a glass reaction vessel equipped with a mechanical stirrer and reflux condenser. The reaction mixture is heated at reflux for a period of about 4 hours. After this time the mixture is stripped of benzene and unreacted phosgene to yield the desired product N-(2-methylsulfonyl-1,3,4-thiadiazol-5-yl)-N-methylcarbamoyl chloride.

EXAMPLE 16

Preparation of N-(2-Methylsulfonyl-1,3,4-thiadiazol-5-yl)-N-methyl-N'-(1,3-dioxan-2-ylmethyl)urea N-(2-Methylsulfonyl-1,3,4-thiadiazol-5-yl)-N-methylcarbamoyl chloride (0.05 mole), N-(1,3-dioxan-2-ylmethyl)amine (0.05 mole), triethylamine (0.07 mole) and benzene (200 ml) are charged into a glass reaction vessel equipped with a mechanical stirrer, thermometer and reflux condenser. The reaction mixture is then heated at reflux for a period of about 4 hours. After this time the mixture is cooled to room temperature and is filtered. The filtrate is washed with water and is dried over anhydrous magnesium sulfate. The dried solution is then stripped of solvent under reduced pressure to yield the desired product N-(2-methylsulfonyl-1,3,4-thiadiazol-5-yl)-N-methyl-N'-(1,3-dioxan-2-ylmethyl)urea.

Additional compounds within the scope of the present invention can be prepared by the procedures detailed in the foregoing examples. In the following examples are given the essential starting materials to prepare the indicated named compounds by the methods heretofore described.

EXAMPLE 15

The dimethyl acetal of 2-chloroacetaldehyde + propandiol-1,2 + ammonia + 2-isopropyl-5-ethylamino-1,3,4-thiadiazole + phosgene = N-(2-isopropyl-1,3,4-thiadiazol-5-yl)-N-ethyl-N'-(4-methyl-1,3-dioxolan-2-ylmethyl)urea.

EXAMPLE 16

The dimethyl acetal of 3-chloropropionaldehyde + butandiol-1,4 + methylamine + 2-methoxy-5-amino-1,3,4-thiadiazole + phosgene = N-(2-methoxy-1,3,4-thiadiazol-5-yl)-N'-(1,3-dioxepan-2-ylethyl)-N'-methylurea.

EXAMPLE 17

The dimethyl acetal of 2-chloroacetaldehyde + butandiol-1,2 + propylamine + 2-cyclohexyl-5-amino-1,3,4-thiadiazole + phosgene = N-(2-cyclohexyl-1,3,4-thiadiazol-5-yl)-N'-(4-ethyl-1,3-dioxolan-3-ylmethyl)-N'-propylurea.

EXAMPLE 18

The dimethyl acetal of 2-chloroacetaldehyde + ethandithiol + methylamine + 2-allyl-5-ethylamino-1,3,4-thiadiazole + phosgene = N-(2-cyclohexyl-1,3,4- thiadiazol-5-yl)-N'-(4-ethyl-1,3-dioxolan-3-ylmethyl)-N'-propylurea.

EXAMPLE 19

The dimethyl acetal of 2-chloroacetaldehyde + propandithiol-1,3 + methylamine + 2-methylsulfinyl-5-propylamino-1,3,4-thiadiazole + phosgene = N-(2-methylsulfinyl-1,3,4-thiadiazol-5-yl)-N-propyl-N'-(1,3-dithian-2-ylmethyl)-N'-methylurea.

EXAMPLE 20

The dimethyl acetal of 2-chloroacetaldehyde + pentandiol-1,2 + methylamine + 2-methyl-5-amino-1,3,4-thiadiazole + phosgene = N-(2-methyl-1,3,4-thiadiazol-5-yl)-N'-(4-propyl-1,3-dioxolan-2-ylmethyl)-N'-methylurea.

Additional compounds within the scope of the present invention are N-(2-methyl-1,3,4-thiadiazol-5-yl)-N'-(1,3-dioxolan-2-ylmethyl)-N'-methylurea, N-(2-ethyl-1,3,4-thiadiazol-5-yl)-N'-(1,3-dioxolan-2-ylmethyl)-N'-methylurea, N-(2-hexyl-1,3,4-thiadiazol-5-yl)-N'-(1,3-dioxolan-2-ylmethyl)-N'-methylurea, N-(2-pent-3-enyl-1,3,4-thiadiazol-5-yl)-N'-(1,3-dioxolan-2-ylmethyl)-N'-methylurea, N-(2-hex-4-enyl-1,3,4-thiadiazol-5-yl)-N'-(1,3-dioxolan-2-ylmethyl)-N'-methylurea, N-(2-chloromethyl-1,3,4-thiadiazol-5-yl)-N'-(1,3-dioxolan-2-ylmethyl)-N'-methylureea, N-(2-tribromomethyl-1,3,4-thiadiazol-5-yl)-N'-(1,3-dioxolan-2-ylmethyl)-N'-methylurea, N-(2$\beta$-bromomethyl-1,3,4-thiadiazol-5-yl)-N'-1,3-dioxolan-2-ylmethyl)-N'-methylurea, N-(2-$\gamma$-chloropropyl-1,3,4-thiadiazol-5-yl)-N'-(1,3-dioxolan-2-ylmethyl)-N'-methylurea, N-(2$\delta$-chlorobutyl-1,3,4-thiadiazol-5-yl)-N' -(1,3-dioxolan-2-ylmethyl)-N'-methylurea, N-(2-cyclopropyl-1,3,4-thiadiazol-5-yl)-N'-(1,3dioxolan-2-ylmethyl)-N'-methylurea, N-(2cyclobutyl-1,3,4-thiadiazol-5-yl)-N'-(1,3-dioxolan-2-ylmethyl)-N'-methylurea, N-(2-cyclopentyl-1,3,4-thiadiazol-5-yl)-N'-(1,3-dioxolan-2-ylmethyl)-N'-methylurea, N-(2-cycloheptyl-1,3,4-thiadiazol-5-yl)-N'-(1,3-dioxolan-2-ylmethyl)-N'-methylurea, N-(2-cyclooctyl-1,3,4-thiadiazol-5-yl)-N'-(1,3-dioxolan-2-ylmethyl)-N'-methylurea, N-(2-ethoxy-1,3,4-thiadiazol-5-yl)-N'-(1,3-dioxolan-2-ylmethyl)-N'-methylurea, N-(2propoxy-1,3,4-thiadiazol-5-yl)-N'-(1,3-dioxolan-2-ylmethyl)-N'-methylurea, N-(2-butoxy-1,3,4-thiadiazol-5-yl)-N'-(1,3-dioxolan-2-ylmethyl)-N'-methylurea, N-(2-pentyloxy-1,3,4-thiadiazol-5-yl)-N'-(1,3-dioxolan-2-ylmethyl)-N'-methylurea, N-(2-hexyloxy-1,3,4-thiadiazol-5-yl)-N'-(1,3-dioxolan-2-ylmethyl)-N'-methylurea, N-(2-ethylthio-1,3,4-thiadiazol-5-yl)-N'-(1,3-dioxolan-2-ylmethyl)-N'-methylurea, N-(2-propylthio-1,3,4-thiadiazol-5-yl)-N'-(1,3-dioxolan-2-ylmethyl)-N'methylurea, N-(2-butylthio-1,3,4-thiadiazol-5-yl)-N'-(1,3-dioxolan-2-ylmethyl)-N'-methylurea, N-(2-pentylthio-1,3,4-thiadiazol-5-yl)-N'-(1,3-dioxolan-2-ylmethyl)-N'-methylurea, N-(2-hexylthio-1,3,4-thiadiazol-5-yl)-N'-(1,3-dioxolan-2 -ylmethyl)-N'-propylurea, N-(2-propylsulfonyl-1,3,4-thiadiazol-5-yl)-N'-(1,3-dioxan-2-ylmethyl)-N'-butylurea, N-(2-butylsulfonyl-1,3,4-thiadiazol-5-yl)-N'-(1,3-dioxan-2-ylmethyl)-N'-pentylurea, N-(2-hexylsulfonyl-1,3,4-thiadiazol-5-yl)-N'-(1,3-dioxan-2-ylmethyl)-N'-hexylurea, N-(2-ethylsulfinyl-1,3,4-thiadiazol-5-yl)-N'-(1,3-dioxan-2-ylmethyl)-N'-methylurea, N-(2-propylsulfinyl-1,3,4-thiadiazol-5-yl)-N'-(1,3-dioxan-2-ylmethyl)-N'-methylurea, N-(2-butylsulfinyl-1,3,4-thiadiazol-5-yl)-N'-(1,3-dioxan-2-ylmethyl)-N'-methylurea, N-(2-hexylsulfinyl-1,3,4 -thiadiazol-5-yl)-N'-(1,3-dioxan-2-ylmethyl)-N'-methylurea, N-(2-t-butyl-1,3,4-thiadiazol-5-yl)-N-methyl-N'-(4-propyl-1,3-dioxepan-2-ylmethyl)-N'-methylurea, N-(2-t-butyl-1,3,4-thiadiazol-5-yl)-N-propyl-N'-(4-butyl-1,3-dioxepan-2-ylmethyl)-N'-methylurea, N-(2-t- butyl-1,3,4-thiadiazol-5-yl)-N-butyl-N'-(4-pentyl-1,3-dioxepan-2-ylmethyl)-N'-methylurea, N-(2-t-butyl-1,3,4-thiadiazol-5-yl)-N-pentyl-N'-(4-hexyl-1,3-dioxepan-2-ylmethyl)-N'-methylurea, N-(2-t-butyl-1,3,4-thiadiazol-5-yl)-N-hexyl-N'-(4,5-dimethyl-1,3-dioxolan-2-ylmethyl)-N'-methylurea, N-(2-t-butyl-1,3,4-thiadiazol-5-yl)-N'-(4,5-diethyl-1,3-dioxolan-2-ylmethyl)-N'-methylurea, N-(2-t-butyl-1,3,4-thiadiazol-5-yl)-N'-(4,5-dipropyl-1,3-dioxolan-2-ylmethyl)-N'-methylurea, N-(2-t-butyl-1,3,4-thiadiazol-5-yl)-N'-(4,5-dihexyl-1,3-dioxolan-2-ylmethyl)-N'-methylurea, N-(2-t-butyl-1,3,4-thiadiazol-5-yl)-N'-(4,7-dimethyl-1,3,dioxepan-2-ylmethyl)-N'-methylurea, N-(2-t-butyl-1,3,44,7,3,4-thiadiazol-5-yl)-N'-(4,7-dibutyl-1,3-dioxepan-2-ylmethyl)-N'-methylurea, N-(2-t-butyl-1,3,4-thiadiazol-5-yl)-N'-(4,7-dihexyl-1,3-dioxepan-2-ylmethyl)-N'-methylurea.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under super-atmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition acording to this invention is illustrated by the following example, in which the quantities are in parts by weight.

Example 21

Preparation of a Dust

| Product of Example 4 | 10 |
|---|---|
| Powdered Talc | 90 |

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an esential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, dessicants, growth inhibitors, and the like in the herbicidal compositions heretofore described. These other materials can comprise from about 5% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4-CPA, 4-CPP, 2,4,5-TB, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon, and the like; symmetrical triazine herbicides such as simazine, chlorazine, atraone, desmetryne, norazine, ipazine, prometryn, atrazine, and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)morpholine 1(chloroacetyl)-piperidine and the like; chlorinated aliphatic acid herbicides such as TCA, dalapon, 2,3-dichloropropionic acid, 2,2,3 -TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxadizolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone, B, propanil and the like.

Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, wild buckwheat kochia, medic, corn cockle, ragweed, sowthistle, coffeeweed, croton, cuphea, dodder, fumitory, groundsel, hemp nettle, knawel, spurge, spurry, emex, jungle rice, pondweed, dog fennel, carpetweed, morningglory, bedstraw, ducksalad and naiad; biennials such as wild carrot, matricaria, wild barley, campion, chamomile, burdock, mullein, roundleaved mallow, bull thistle, hounds-tongue, moth mullein and purple star thistle; or perennial ryegrass, quackgrass, Johnsongrass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail and winter-cress.

Similarly, such weeds can be classsified as broadleaf or grassy weeds. It is economicallly desirable to control the growth of such weeds without damaging beneficial plants or livestock.

The new compounds of this invention are particularly valuable for weed control because they are toxic to many species and groups of weeds while they are relatively non-toxic to many beneficial plants. The exact amount of compound required will depend on a variety of factors, including the hardiness of the particular weed species, weather, type of soil, method of application, the kind of beneficial plants in the same area and the like. Thus, while the application of up to only about one or two ounces of active compound per acre may be sufficient for good control of a light infestation of weeds growing under adverse conditions, the application of ten pounds or more of an active compound per acre may be required for good control of a dense infestation of hardly perennial weeds growing under favorable conditions.

The herbicidal toxicity of the new compounds of this invention was demonstrated by experiments carried out for the pre-emergence control of a variety of weeds. In these experiments small plastic greenhouse pots filled with dry soil were seeded with the various weed seeds. Twenty-four hours or less after seeding the pots were sprayed with water until the soil was wet and the product or Example 4 formulated as aqueous emulsions of acetone solutions containing emulsifiers were sprayed at a rate of 10 pounds per acre on the surface of the soil.

After spraying, the soil containers were placed in the greenhouse and provided with supplementary heat as required and daily or more frequent watering. The plants were maintained under these conditions for a period of 27 days. At 21 and 27 days after treatment the condition of the plants and the degree of injury to the plants was rated on a scale of 0 to 10, as follows: 0 = no injury, 1,2 = slight injury, 3,4 = moderate injury, 5, 6 = moderately severe injury, 7,8,9 = severe injury and 10 = death. The herbicidal effectiveness is demonstrated by the following data in Table I.

The herbicidal activity of the compounds of this invention was also demonstrated by experiments carried out for the post-emergence control of a variety of weeds. In these experiments the product of Example 4 was formulated as aqueous emulsions and sprayed at a rate of 10 pounds per acre on the foliage of the weed species that have attained a prescribed size. After spraying, the plants were placed in a greenhouse and watered daily or more frequently. Water was not applied to the foliage of the treated plants. The severity of the injury was determined 15 and 27 days after treatment and was rated on the scale of from 0 to 10 heretofore described. The effectiveness as a post-emergence herbicide is demonstrated by the data in Table I.

TABLE I

| Weed Species | INJURY RATING | | | |
| --- | --- | --- | --- | --- |
| | Pre-Emergence | | Post-Emergence | |
| | 21 days | 27 days | 15 days | 27 days |
| Yellow Nutsedge | 4 | 3 | 8 | 9 |
| Wild Oats | 9 | 10 | 10 | 10 |
| Jimsonweed | 10 | 10 | 10 | 10 |
| Velvetleaf | 10 | 10 | — | — |
| Johnsongrass | 6 | 9 | 10 | 9 |
| Pigweed | 7 | 9 | 10 | 10 |
| Mustard | 10 | 10 | 10 | 10 |
| Yellow Foxtail | 8 | 9 | 8 | 10 |
| Barnyardgrass | 9 | 10 | 10 | 10 |
| Crabgrass | 9 | 10 | 10 | 10 |
| Cheatgrass | 9 | 10 | — | — |
| Morningglory | 9 | 10 | 10 | 10 |
| Bindweed | — | — | 4 | 9 |

I claim:

1. A herbicidal composition comprising an inert carrier and, as an essential active ingredient, in a quantity toxic to weeds, a compounds of the formula

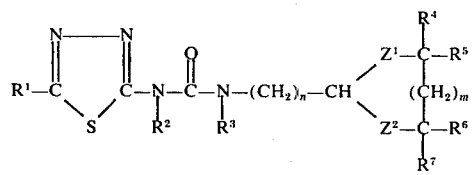

wherein $R^1$ is selected from the group consisting of lower alkyl, lower alkenyl, lower chloroalkyl, lower bromoalkyl, trifluomethyl, cycloalkyl of from 3 to 7 carbon atoms, lower alkoxy, lower alkylthio, lower alkylsufonyl, and lower alkylsulfinyl; $Z^1$ and $Z^2$ are independently selected from the group consisting of oxygen and sulfur; $R^2$, $R^3$, $R^4$, $R^5$, $R^6$, and $R^7$ are each selected from the group consisting of hydrogen and lower alkyl; $m$ is an integer from 0 to 2; and $n$ is the integer 1 or 2.

2. A method of controlling weeds which comprises contacting the weeds with a herbicidal composition of claim 1.

* * * * *